US00PP27490P3

(12) United States Plant Patent
Klemm et al.

(10) Patent No.: US PP27,490 P3
(45) Date of Patent: Dec. 20, 2016

(54) ***CALIBRACHOA* PLANT NAMED 'KLECA15388'**

(50) Latin Name: ***Calibrachoa* sp.**
Varietal Denomination: KLECA15388

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 184 days.

(21) Appl. No.: 14/121,565

(22) Filed: Sep. 18, 2014

(65) Prior Publication Data
US 2015/0020276 P1 Jan. 15, 2015

(51) Int. Cl.
*A01H 5/02* (2006.01)

(52) U.S. Cl.
USPC ..... Plt./413
CPC ..... *A01H 5/02* (2013.01)

(58) Field of Classification Search
USPC ..... Plt./413
See application file for complete search history.

*Primary Examiner* — Keith Robinson
(74) *Attorney, Agent, or Firm* — James M. Weatherly; Barbara Campbell; Cochran Freund & Young LLC

(57) ABSTRACT

A new *Calibrachoa* plant particularly distinguished by having a single yellow flower color and a semi-upright plant habit, is disclosed.

1 Drawing Sheet

Genus and species: *Calibrachoa* sp.
Variety denomination: 'KLECA15388'.

BACKGROUND OF THE NEW PLANT

The present invention comprises a new and distinct variety of *Calibrachoa*, botanically known as *Calibrachoa* sp., and hereinafter referred to by the variety name 'KLECA15388'. 'KLECA15388' originated from a cross-pollination between the female parent 'CA-2013-0238' which is an offspring of the varieties SUPERBELLS 'Lemon Slice' (U.S. Plant Pat. No. 24,353 also known as 'USCAL5302M') (female) and SUPERBELLS 'Cherry Star' (U.S. Plant Pat. No. 23,232 also known as 'USCAL91001') (male) and the male parent 'CA-2013-0356' (unpatented) which is an offspring of the varieties SUPERBELLS 'Lemon Slice' (female) and the proprietary male *calibrachoa* 'CA-2010-2248' (unpatented).

The original intention of the cross was to breed a variety with inflorescences exhibiting a star-shaped pattern as described in U.S. application Ser. No. 13/791,614. Therefore, in 2012 the variety 'Lemon Slice' (U.S. Plant Pat. No. 24,353 also known as 'USCAL5302M'), which comprises inflorescences with a star-shaped pattern, was crossed with the variety SUPERBELLS 'Cherry Star' (U.S. Plant Pat. No. 23,232 also known as 'USCAL91001'). In a further cross the variety 'Lemon Slice' was crossed with Applicant's own *calibrachoa* breeding line 'CA-2010-2248'. It should be noted that both male parents did not exhibit the star shaped pattern, following the method of U.S. application Ser. No. 13/791,614. The seeds from both crosses were germinated and 100 seedlings each were cultivated until flowering. Of the resulting 100 seedlings, none of the progeny exhibited inflorescences with a star shaped pattern, as described in U.S. application Ser. No. 13/791,614.

From the first progeny the seedling 'CA-2013-0238' was selected and crossed with the seedling 'CA-2013-0356', which was selected from the second progeny. From this cross an offspring of 100 seedlings was grown and observed for a star-shaped pattern. However, none of the progeny showed this star pattern.

Furthermore, in 2012 the variety 'Lemon Slice' was crossed into 52 further different *Calibrachoa* varieties and breeding lines, which all did not exhibit the star-shaped pattern as described in U.S. application Ser. No. 13/791,614. In 16 of these crosses Lemon Slice was used as the male parent and in further 36 crosses 'Lemon Slice' was used as the female parent. Additionally, in one cross 'Lemon Slice' was self-pollinated. In 2013, 5,300 seedlings resulting from these crosses, were grown to flower and selected for the star-shaped pattern. 100 individuals progeny were evaluated. However, none of the offspring showed the star-shaped pattern. Also the subsequent backcrossing of selected $F_1$ seedlings into 'Lemon Slice' as well as crosses among them did not result in any progeny exhibiting the star-shaped pattern In July and August of 2013, a single plant line was selected, having a single yellow color and subsequently named 'KLECA15388'. In July and August of 2013, 'KLECA15388' was first vegetatively propagated by tip cuttings in Stuttgart, Germany. 'KLECA15388' was found to reproduce true to type in successive generations of asexual propagation via shoot tip cuttings.

SUMMARY

The following are the most outstanding and distinguishing characteristics of this new variety when grown under normal horticultural practices in Stuttgart, Germany.

1. A single yellow color flower color; and
2. A semi-upright plant habit.

DESCRIPTION OF THE PHOTOGRAPH

This new *Calibrachoa* plant is illustrated by the accompanying photograph which shows flowers grown in a pot.

The photograph is of a six-month-old plant grown in an outdoor environment in Stuttgart, Germany in September 2014.

The colors shown are as true as can be reasonably obtained by conventional photographic procedures.

DESCRIPTION OF THE NEW VARIETY

The following detailed descriptions set forth the distinctive characteristics of 'KLECA15388'. The data which define these characteristics were collected from asexual reproductions carried out in Stuttgart, Germany. Data was collected on 4.5 month-old plants grown in Stuttgart, Germany in September 2014. Color references are to The R.H.S. Colour Chart of The Royal Horticultural Society of London (R.H.S.), 5$^{th}$ edition (2007).

Classification:
- *Family*.—Solanaceae.
- *Species*.—*Calibrachoa* sp.
- *Common name*.—*Calibrachoa*.
- *Parentage*.—Female parent: 'CA-2013-0238' which is an offspring of the varieties SUPERBELLS 'Lemon Slice' (U.S. Plant Pat. No. 24,353) (female) and SUPERBELLS 'Cherry Star' (U.S. Plant Pat. No. 23,232 also known as 'USCAL91001') (male). Male parent: 'CA-2013-0356' which is an offspring of the varieties SUPERBELLS 'Lemon Slice' (female) and 'CA-2010-2248' (male).

Plant description:
- *Life cycle*.—Annual.
- *Form*.—Semi-upright.
- *Habit*.—Semi-upright.
- *Height* (*from soil line to top of foliage*).—12.0 cm.
- *Spread*.—28.0 cm.

Propagation: Vegetatively propagated.
- *Type cuttings*.—Tip cuttings.
- *Time to initiate roots*.—21 days.
- *Length of shoot*.—14.0 cm.
- *Time to produce a rooted cutting*.—3 weeks.

Stems:
- *Stem color*.—RHS 144B.
- *Pubescence*.—Absent.
- *Stem description*.—Stem diameter: Include side shoots: 6.0 cm (stem only: 0.2 cm).
- *Stem length*.—12.0 cm. From soil line to first node: 2.1 cm. Total length: 14.0 cm.
- *Internode length*.—2.4 cm.

Leaves:
- *Arrangement*.—Alternate, simple, sessile.
- *Shape*.—Broadly elliptic.
- *Apex*.—Obtuse to slightly acute.
- *Base*.—Attenuate.
- *Margin*.—Entire.
- *Texture* (*both surfaces*).—Smooth.
- *Surface pubescence*.—Absent on both upper and lower surfaces.
- *Variegation*.—Absent.
- *Venation*.—Pinnate.
- *Venation color*.—Upper surface: RHS 143B. Lower surface: RHS 143C.
- *Length*.—2.7 cm.
- *Width*.—0.8 cm.
- *Color*.—Upper surface: RHS 137B. Lower surface: RHS 137D.
- *Fragrance*.—Absent.

Flowers: Single flowers.
- *Flowering habit*.—Flower attitude is semi-erect, single, axillary.
- *Flower type*.—Determinate inflorescence.
- *Flowering requirements*.—A minimum of light sun is required.
- *Duration of flowers*.—5 days.
- *Corolla*.—Smooth texture.
- *Shape*.—Funnel-shaped.
- *Fragrance*.—Absent.

Flower buds:
- *Surface*.—Smooth.
- *Length*.—1.9 cm.
- *Diameter*.—0.6 cm.
- *Shape*.—Irregular to oblong.
- *Color*.—RHS 7D.

Peduncle:
- *Length*.—1.5 cm.
- *Diameter*.—0.1 cm.
- *Color*.—RHS N144A.
- *Texture*.—Smooth.
- *Anthocyanin color*.—Absent.

Flower description:
- *Flower depth*.—2.7 cm.
- *Flower tube length*.—1.5 cm.
- *Flower tube diameter*.—0.7 cm.
- *Flower diameter*.—2.5 cm.
- *Pedicel color*.—RHS 142B.
- *Pedicel length*.—1.0 cm.
- *Pedicel diameter*.—1.0 mm.
- *Calyx*.—Funnel-shaped.
- *Calyx lobe length*.—1.5 cm.
- *Calyx lobe width*.—1.0 cm.
- *Degree of lobing*.—Weak.

Sepals:
- *Quantity per flower*.—5.
- *Shape*.—Broad Lanceolate.
- *Apex*.—Acute.
- *Base*.—Fused along lower half. Color of base at lower surface: RHS 144B. Color of base at upper surface: RHS 144C.
- *Margin*.—Entire.
- *Length*.—1.2 cm.
- *Diameter*.—0.2 cm.
- *Texture* (*both surfaces*).—Smooth.
- *Sepal color*.—Upper surface: RHS 147A. Lower surface: RHS 147B.

Petals:
- *Shape*.—Heart-shaped.
- *Length*.—1.6 cm.
- *Apex*.—Obverse.
- *Margin*.—Entire, weak indulation.
- *Base*.—Open and fused into the tube.
- *Texture* (*both surfaces*).—Smooth.
- *Pubescence*.—Absent.
- *Lobe length*.—1.4 cm.
- *Lobe width*.—1.1 cm.
- *Color*.—Lobe color: Upper surface: RHS 7A. Lower surface: RHS 10A. Corolla tube color: Inner: RHS 12A. Outer: RHS 11A.
- *Conspicuousness of veins on upper side of corolla lobe*.—Weak.
- *Fragrance*.—Absent.

Reproductive organs:
- *Stamen number*.—5.
- *Stamen color*.—Anther color: RHS 14B. Anther length: 1.5 mm. Anther shape: Ellipsoidal. Filament color: RHS 1B. Filament length: 9.0 mm. Pollen color: RHS 14B. Amount of pollen: Scarce.

*Ovary*.—Placenta arrangement: Ovate. Ovary color: RHS N144C. Pistil number: 1. Pistil length: 0.1 cm. Stigma color: RHS 142A. Style length: 0.9 cm. Style color: RHS 142B.

Seed and fruit description: Unavailable.

COMPARISON WITH PARENTAL LINES AND KNOWN VARIETY

'KLECA15388' is distinguished from its female and male parents as described in Table 1:

TABLE 1

Comparison with Parental Lines

| Trait | Variety 'KLECA15388' | Female Parent 'CA-2013-0238' | Male Parent 'CA-2013-0356' |
|---|---|---|---|
| Flower color | RHS 7A | RHS 1C and RHS 2A | RHS 58B |

'KLECA15388' is most similar to the *Calibrachoa* plant named SUPERBELLS 'Lemon Slice' (U.S. Plant Pat. No. 24,353 also known as 'USCAL5302M'). Differences between the two varieties are described in Table 2:

TABLE 2

Comparison with Similar Variety

| Trait | Variety 'KLECA15388' | Commercial line SUPERBELLS 'Lemon Slice' |
|---|---|---|
| Flower color | Single color yellow | Bicolor: yellow and white |

We claim:

1. A new and distinct variety of *Calibrachoa* plant named 'KLECA15388' as illustrated and described herein.

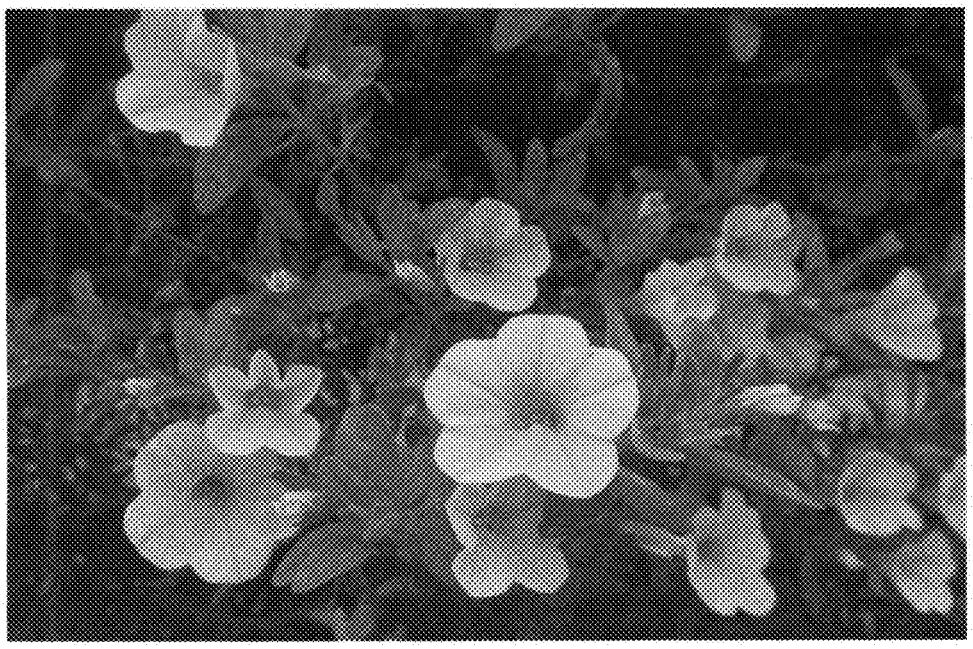

* * * * *